(12) United States Patent
Woehr

(10) Patent No.: US 8,801,663 B2
(45) Date of Patent: Aug. 12, 2014

(54) PROTECTIVE DEVICE FOR AN INJECTION NEEDLE

(75) Inventor: Kevin Woehr, Felsberg (DE)

(73) Assignee: B. Braun Melsungen AG, Melsungen (DE)

( * ) Notice: Subject to any disclaimer, the term of this patent is extended or adjusted under 35 U.S.C. 154(b) by 82 days.

(21) Appl. No.: 13/381,287

(22) PCT Filed: Jul. 2, 2010

(86) PCT No.: PCT/EP2010/003997
§ 371 (c)(1),
(2), (4) Date: Jan. 31, 2012

(87) PCT Pub. No.: WO2011/000570
PCT Pub. Date: Jan. 6, 2011

(65) Prior Publication Data
US 2012/0130321 A1    May 24, 2012

(30) Foreign Application Priority Data

Jul. 2, 2009    (DE) .................... 20 2009 009 119 U

(51) Int. Cl.
*A61M 5/00*     (2006.01)
*A61M 25/06*    (2006.01)
*A61M 5/32*     (2006.01)

(52) U.S. Cl.
CPC ....... *A61M 5/3273* (2013.01); *A61M 2005/325* (2013.01); *A61M 25/0618* (2013.01); *A61M 25/0631* (2013.01)
USPC ......................................................... 604/110

(58) Field of Classification Search
USPC ......................................... 604/110, 192, 198
See application file for complete search history.

(56) References Cited

U.S. PATENT DOCUMENTS

| 4,929,241 | A  | * | 5/1990  | Kulli ............................. 604/263 |
| 5,053,017 | A  | * | 10/1991 | Chamuel ....................... 604/192 |
| 6,210,373 | B1 |   | 4/2001  | Allmon |
| 6,749,588 | B1 | * | 6/2004  | Howell et al. ............. 604/164.08 |
| 7,637,887 | B2 | * | 12/2009 | Woehr .......................... 604/110 |
| 2007/0270754 | A1 | * | 11/2007 | Soderholm et al. ...... 604/164.08 |
| 2008/0243086 | A1 |   | 10/2008 | Hager et al. |

FOREIGN PATENT DOCUMENTS

| DE | 203 16 804 U1 | 3/2005 |
| EP | 0 750 915 A2  | 1/1997 |
| EP | 1 110 571 A1  | 6/2001 |

OTHER PUBLICATIONS

International Search Report completed Aug. 27, 2010 and mailed Sep. 6, 2010 from corresponding International Application No. PCT/EP2010/003997 filed Jul. 2, 2010 (8 pages).
Written Opinion completed Aug. 27, 2010 and mailed Sep. 6, 2010 from corresponding International Application No. PCT/EP2010/003997 filed Jul. 2, 2010 (6 pages).

* cited by examiner

*Primary Examiner* — Aarti B Berdichevsky
(74) *Attorney, Agent, or Firm* — Klein, O'Neill & Singh, LLP

(57) ABSTRACT

A protective device for an injection or infusion needle is provided comprising a needle hub at the proximal end of the needle, on whose shaft a protective member for the needle tip is displaceable, the protective member having an engaging section which engages with the needle shaft to prevent the protective member from being displaced beyond the needle tip, wherein the protective member is surrounded by a tube whose diameter is locally reduced or deformed such that the protective member is confined in the tube.

18 Claims, 7 Drawing Sheets

PROTECTIVE DEVICE FOR AN INJECTION NEEDLE

CROSS-REFERENCE TO RELATED APPLICATIONS

This is a national phase application under 35 U.S.C. §371 of PCT Application No. PCT/EP2010/003997, filed Jul. 2, 2010, which claims the benefit of German application No. 20 2009 009 119 8 filed Jul. 2, 2009, the contents of each of which are expressly incorporated herein by reference.

FIELD OF ART

The present disclosure relates to a protective device for an injection or infusion needle comprising a protective member surrounded by a tube.

BACKGROUND

DE 203 15 872 U1 discloses a protective device with low production costs, wherein the protective member as described in one of the preferred embodiments as a spring clip is surrounded by a shrink tube engaging the protective member by radial tension. Due to this, the mobility of the protective member along the needle shaft is affected, above all when the protective member has two opposite resilient arms whose angled distal ends abut at the needle shaft, wherein the arms of the protective member are biased against the needle by the shrink tube.

SUMMARY

The present method, system and device are based on the object of designing a protective device with low production costs such that the protective member is easily displaceable along the needle.

This object is achieved by a protective device, wherein the tube surrounding the protective member has a diameter which is only locally reduced or deformed such that the protective member is confined within the tube.

Preferably the tube is a shrink tube which is locally deformed by heat action. The shrink tube does not thereby apply radial tension to the arms of the protective member and the protective member can be displaced easily together with the shrink tube along the needle shaft. The shrink tube mounted on the protective member limits the possible relative axial movement of the protective member and the shrink tube to within the shrink tube.

Advantageous embodiments of the present method, system and device are to be found in the following detailed description, drawings and claims.

The protective device comprises a tube, preferably a shrink tube, which is deformed not overall but only locally at one position or at a plurality of positions, for example at the distal and proximal ends or end portions of the shrink tube which protrude over the ends of the protective member. Here, the diameter of the shrink tube is reduced, or changed, locally by heat action such that the protective member is reliably confined within the shrink tube or the shrink tube is reliably mounted and retained on the protective member due to these diametrally reduced or changed areas of the shrink tube.

Hereby, the protective tube can have an inner diameter, for example between diametrally reduced end portions, which is larger than the maximum radial dimension of the protective member, so the protective member is confined and thereby retained in the shrink tube only by axial abutment at the diametrally reduced ends or end portions thereof.

On account of the merely local deformation of the shrink tube, a protective device results which is very cost-effective to manufacture and in which the protective member is not negatively affected by the mounted shrink tube and the shrink tube forms a grip part for handling the protective member. The shrink tube can also be regarded as a protective tube protecting the protective member from being contacted by the fingers of an operator.

Instead of a tube consisting of a material which is shrinkable by heat action a tube consisting of another material, plastic material or metal, can also be used, this material then being locally deformable by various known methods. The material can for example be plastically deformable by pressure action.

Further aims, advantages, features and possible applications of the present method, system and device become apparent from the following description of the embodiments with reference to the drawings. Hereby, all the features described and/or shown diagrammatically form the subject matter of the present method, system and device in themselves or in any meaningful combination, and independently of their summary in the claims and of the back-referencing of the claims.

BRIEF DESCRIPTION OF THE FIGURES

The present method, system and device are explained in more detail below with reference to the drawings, wherein reference is made to the preferred embodiment of a shrink tube.

DETAILED DESCRIPTION

Figure 1:
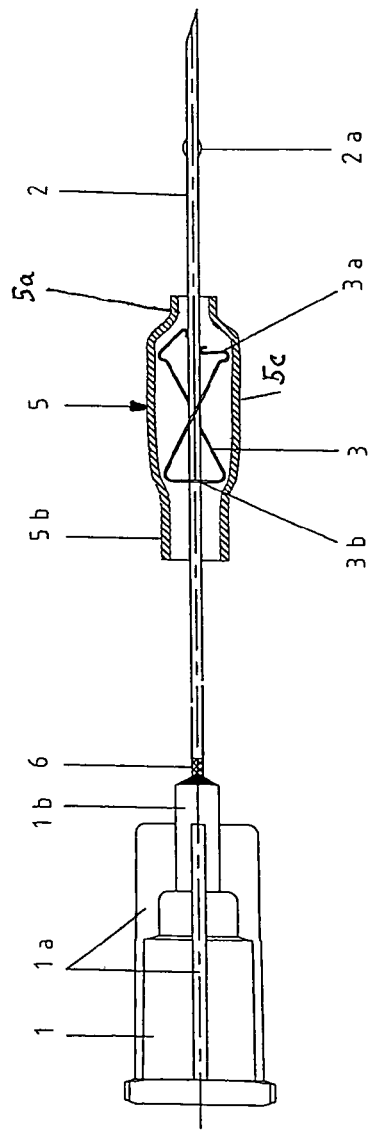
FIG. 1 shows a side view of a needle hub with a needle and the protective device mounted thereon in an assembly position in longitudinal section.

In the Figures, reference numeral 1 designates a needle hub in which a hollow needle 2 is fixed. On the shaft of the needle 2 a protective member 3 is displaceable which, in the embodiment shown, is formed in the form of a spring clip having crossing arms, one arm of which abuts at one side and the other arm of which abuts at the opposite side of the needle shaft by means of angled free end portions 3a. Near the tip of the needle 2 a diametral enlargement 2a is formed, for example by a slight crimping of the hollow needle, so that during displacement of the protective member 3, the aperture formed in the proximal transverse wall 3b thereof cannot be displaced beyond this radial projection 2a and the protective member is held in the protective position in FIG. 3 such that it cannot be displaced beyond the needle tip.

Figure 2:
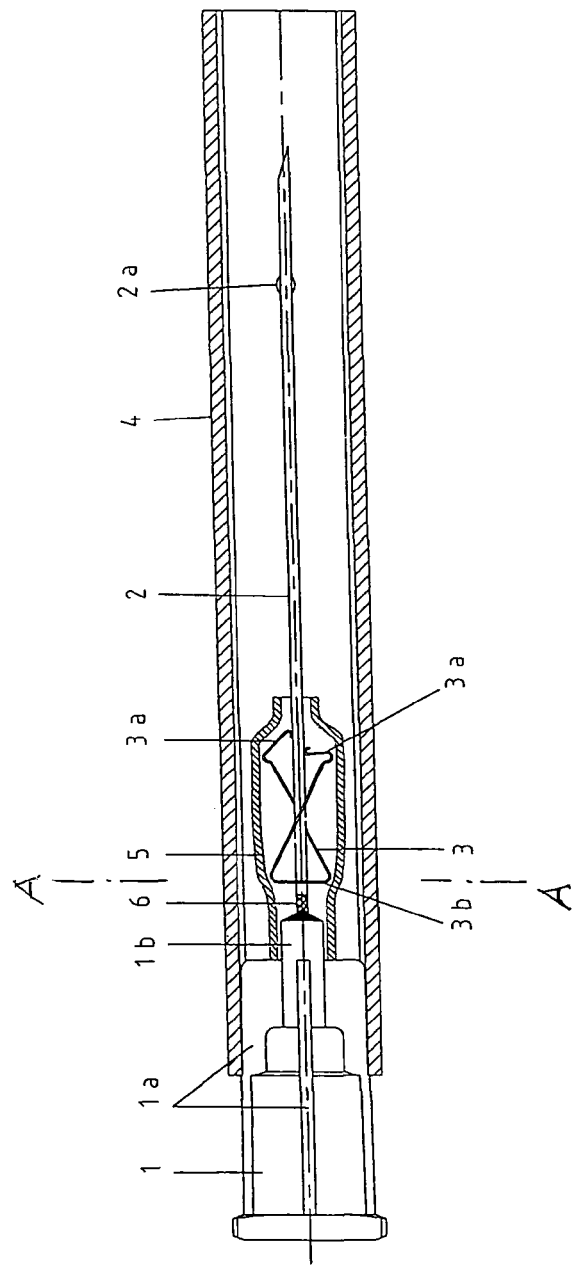
FIG. 2 shows a side view of a needle hub with a needle with a further protective device disposed thereon in a ready position in longitudinal section.

At the needle hub 1, radially protruding ribs 1a can be formed, on which a protective cap 4 represented in FIG. 2 can be attached. Reference numeral 1b designates a distally protruding hub portion on the needle hub 1, which has a smaller diameter than the needle hub 1 and protrudes over the ribs 1a in a distal direction. A syringe or infusion device can be inserted in the needle hub 1.

Figure 1A:
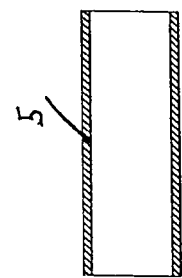
FIG. 1a shows the shrink tube in its initial position in longitudinal section.

The protective member 3 is surrounded by a shrink tube 5, which before assembly has essentially the same diameter and the same wall thickness throughout, as FIG. 1a shows. The shrink tube can be easily displaced over the protective member 3. For this, in its initial position in FIG. 1a the shrink tube 5 advantageously has an inner diameter that is larger than the maximum radial dimension of the protective member 3.

During assembly of the shrink tube 5, the protective member 3 can be located on the needle shaft 2, for example, approximately in the intermediate position shown in FIG. 1, whereupon after the displacement of the shrink tube 5 heat is applied radially from the outside to the ends or end portions 5a and 5b of the shrink tube which protrude over the ends of the protective member 3, such that only these end portions 5a and 5b which protrude over the protective member are reduced in diameter.

Due to specific heat action on the circumference of the shrink tube 5 only at the end portions 5a and 5b, the middle area 5c of the shrink tube maintains its original diameter, so in its assembly position in FIG. 1 the shrink tube 5 can have a radial clearance relative to the protective member 3. The protective member is only restrained from axial movement within the shrink tube 5 by axial abutment at the distal and proximal end in the shrink tube 5 such that it is free to move back and forth within the shrink tube 6 whilst being reliably confined and retained therein as it cannot move out of the shrink tube 5.

Figure 8A:
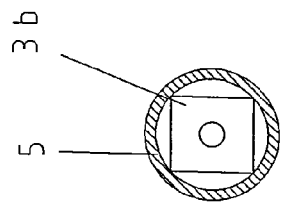
FIGS. 8a-b show sectional views of the shrink tube having a protective member therein without showing the needle.

It is also possible to dimension the shrink tube in relation to the protective member such that the shrink tube abuts lightly at the circumference of the protective member or only at one part of the circumference of the protective member and does not exert any radial tension thereon. Such a design of the shrink tube is indicated in FIG. 2. In the embodiment according to FIG. 2, the proximal transverse wall 3b of the protective member has a rectangular shape, while the shrink tube can have a circular diameter so that the shrink tube can abut only at the corners of the rectangular transverse wall 3b, as FIG. 8a shows. If the shrink tube abuts only at the four corners of the rectangular transverse wall 3b of the protective member under a certain tension, this results in a safeguard against twisting of the protective member 3 relative to the shrink tube 5 without the function of the protective member being otherwise negatively affected, because the arms of the protective member lie unrestrained with radial clearance inside the shrink tube and the shrink tube does not exert any radial tension on the arms of the protective member.

Figure 8B:
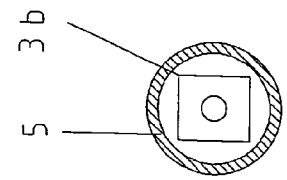

FIG. 8b shows an embodiment in which, in contrast to the embodiment of FIG. 8a, the diameter of the deformed shrink tube 5 in the area of the proximal transverse wall 3b is larger than the maximum radial dimension of the protective member or of the proximal transverse wall 3b thereof. The sectional view in FIG. 8a corresponds to the intersection line A-A given in FIG. 2 without a representation of the needle.

Figure 6:
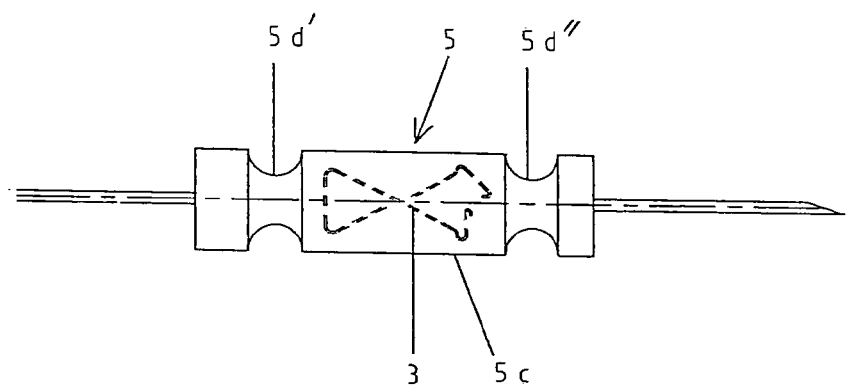
FIG. 6 shows a further design of the shrink tube in a side view.
Figure 7:
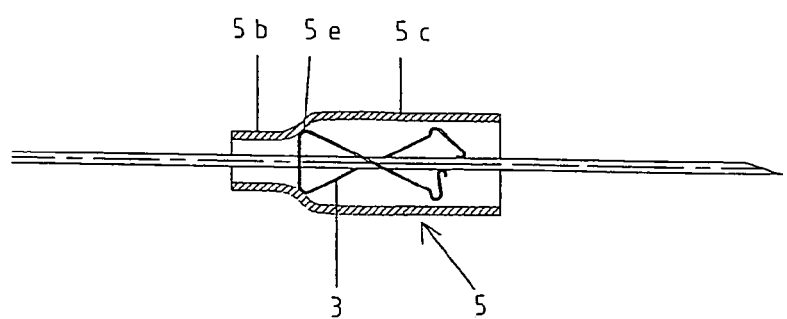
FIG. 7 shows a further design of the shrink tube in longitudinal section.

Thus the protective member can lie completely unrestrained in the deformed shrink tube 5 as indicated in FIG. 6 and FIG. 8b, or partly abut at the shrink tube in the radial direction, as FIG. 7 and FIG. 8a show. However, it is also possible for the protective member to abut at the shrink tube over the length of the protective member or at the ends thereof, although without radial tension, as is indicated in FIG. 1.

Figure 3:
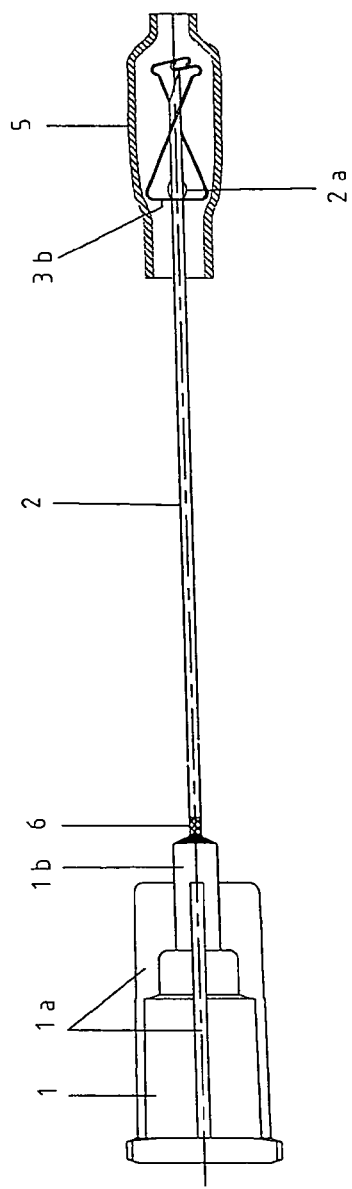
FIG. 3 shows a side view of a needle hub with a needle and the protective device disposed thereon with the protective member in the protective position.

Preferably, the shrink tube 5, which is made of plastic, has a wall thickness or consistency due to which it is relatively stiff, so that the middle area 5c of the shrink tube maintains its shape even when the shrink tube is grasped by the fingers of a hand and the protective member is displaced by means of the shrink tube into the protective position in FIG. 3.

The shrink tube 5 can be elastic; however, it preferably has enough stiffness such that the circumference of the shrink tube in the middle area 5c is not compressed when touched during handling.

Especially in the proximal area, the end portion 5b of the shrink tube 5 is diametrally reduced to have such a longitudinal section that the end portion 5b of the shrink tube holds the protective member at a predetermined distance from the front end of the ribs 1a. Hereby, a distance holder is formed by the end portion 5b between protective member 3 and needle hub 1, which distance holder prevents part of the adhesive from possibly being able to reach the protective member 3 during hardening of the adhesive holding the needle 2 in the needle hub 1. FIG. 1 shows an adhesive coating 6 on the circumference of the needle 2. If the adhesive hardens on the needle circumference as a film and a part of the adhesive could reach the area between the opening in the proximal transverse wall of the protective member and the needle circumference, this would cause the protective member to become jammed. The distance holder in the form of the end portion 5b prevents such jamming at the protective member from being able to occur, because the proximal transverse wall 3b thereof has enough distance from the distal end of the needle hub.

In the representation in FIG. 2, the diametrally reduced end portion 5b of the shrink tube can be arranged with a radial clearance over the hub portion 1b of the needle hub 1. Alternatively, an abutting arrangement without a radial clearance is possible. In the case of a large reduction in the diameter of the end portion 5b, as FIG. 4b shows, this end portion can also abut at the front end of the hub portion 1b.

For such an embodiment, a shrink tube is used which has a correspondingly small diameter in its initial shape, because during the manufacture of a shrink tube it is expanded by an expansion process out of its extruded shape. Under heat action, the tube so expanded then shrinks back down as far as its extruded shape.

Figure 4A:
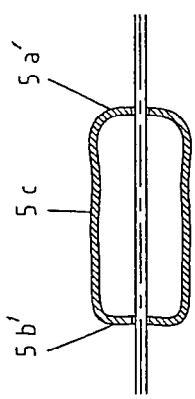
FIGS. 4a-c show different designs of the shrink tube in longitudinal section.

In FIGS. 1 to 3, the diametrally reduced end portions of the shrink tube are represented as longitudinal sections 5a and 5b. However, it is also possible to reduce only the ends of the shrink tube radially inwardly, such that essentially a transverse wall 5a' or 5b' results at the distal and proximal ends of the shrink tube 5, between which ends the protective member 3 is held. FIG. 4a shows such a shape of the shrink tube which can be formed by flanging the tube end inwards by heat forming.

Figure 4B:
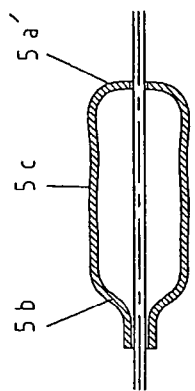

It is also possible to reduce the diameter of the distal and proximal ends of the shrink tube 5 in various forms by various methods, so that, for example at the proximal end, an end portion 5b is formed as the distance holder and at the distal end a sleeve essentially closed by a transverse wall 5a' is formed around the protective member 3, as represented in FIG. 4b. Hereby, the end portion 5b is formed by a shrinking process and the transverse wall 5a' is formed by flanging.

The diametrally reduced ends or end portions 5a, 5a', 5b and 5b' can be designed such that they surround the needle 2 and the diametral enlargement 2a thereof with enough clearance, wherein the diametrally greatly reduced distal end of the shrink tube simultaneously serves as protection against the emergence of blood adhering to the needle tip.

Figure 4C:
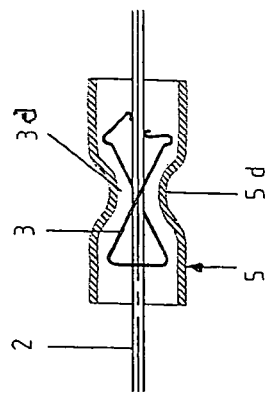

FIG. 4c shows a further embodiment of the shrink tube which is also shrunk in its middle area by annular heat action, such that a constriction 5d arises in the middle area. Such a constriction at 5d is expedient above all when a protective member 3 with intersecting arms is used, in which, in the middle area between proximal and distal end, a free space 3d results into which the constriction 5d can extend for holding the shrink tube 5 axially relative to the protective member 3. In such an embodiment with a constriction 5d in the middle area, it is possible to omit a diametral reduction at the ends of the shrink tube or only at one end of the shrink tube, because due to the tapering 5d, there is enough axial fixation of the shrink tube 5 relative to the protective member 3.

According to a further embodiment, a shrink tube shown in FIG. 6 can be provided with an annular radial constriction 5d' and 5d'' in the area of its ends, between which the protective member is held in the axial direction, possibly also with clearance in the axial direction.

FIG. 7 shows a modified embodiment in which the proximal end of the shrink tube is diametrally reduced and the shrink tube remains unchanged in diameter on the distal side, so that the protective tube 5 deformed in this way forms a grip part for the protective member 3, by means of which the protective member can be displaced forwards into the distal protective position.

In such an embodiment according to FIG. 7, it is expedient to form the radial deformation in the proximal end portion of the shrink tube such that an approximately funnel-shaped transition 5e results between the diametrally reduced end portion 5b and the nondeformed portion 5c, wherein during assembly this funnel-shaped portion 5e can be jammed or wedged with the proximal transverse wall 3b of the protective member to prevent the protective member from being able to move out of the representation in FIG. 7, to the right in the distal direction relative to the shrink tube. The jamming or wedging of the proximal transverse wall 3b takes place in the partly shrunk portion 5e and thus forms a retainer in the shrink tube 5.

Figure 5A:
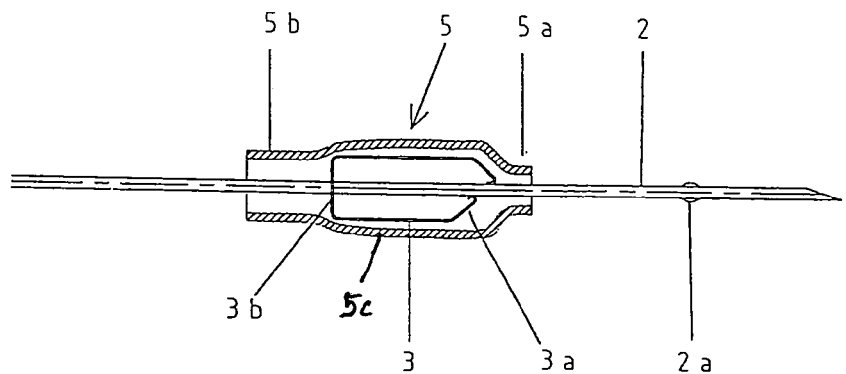
FIGS. 5a-b show two further embodiments of protective members in longitudinal section.

The protective member 3 can be formed in various ways. For example, arms can be provided extending from a proximal rear wall 3b approximately parallel to the needle shaft 2, wherein at least one of the arms is provided with an angled end portion 3a for blocking the needle tip in the protective position, which end portion 3a prevents displacement of the protective member 3 out of the protective position in the proximal direction. FIG. 5a shows such an embodiment. Furthermore, it is also possible to design the protective member 3 as a sleeve with a proximal transverse wall 3b, wherein for such an embodiment, on the proximal side of the protective member 3 in the protective position, a retaining means must be provided on the needle shaft so that the sleeve, which is open on the distal side and surrounds and covers the needle tip in the protective position, cannot be displaced out of the protective position in the proximal direction. Such an embodiment of a protective member in sleeve form with a retainer on the proximal side is known, for example, from EP 1 513 578.

Figure 5B:
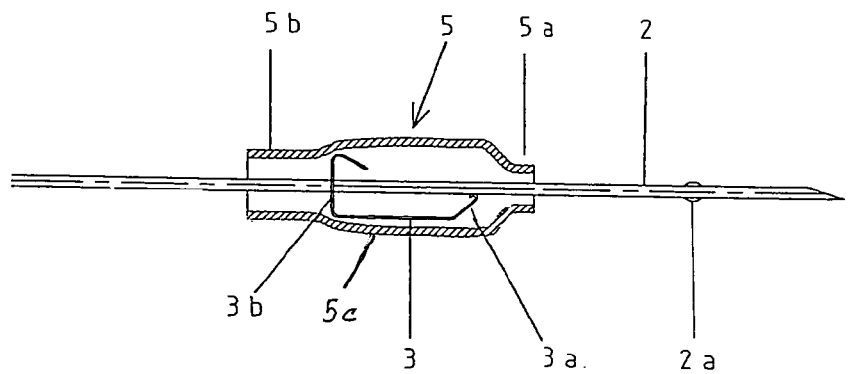

Further embodiments of protective members which can be surrounded by a shrink tube as described, are represented in several variants in WO 99/08742. Another embodiment of a protective member can be formed from only one arm, which extends parallel to the needle shaft from a proximal transverse wall 3b having an opening through which the needle extends, and which has an angled end for blocking the needle tip, as FIG. 5b shows.

Further embodiments of protective members may be taken from U.S. Pat. No. 7,637,887. This type of protective member has a sleeve on its proximal end and arms or an arm attached to and extending distally of the sleeve. This type of protective member can be used not only with a needle with a curved tip but also with straight needles as described below.

In an engagement means with the radial projection at the needle shaft, this radial projection can have the form of a crimping of the needle shaft which is indented on two sides and protrudes on the other two sides. According to another embodiment, this radial projection can also have the shape only of a bead of the needle shaft which has a predetermined distance from the needle tip. A further embodiment can also have only a projection or a crimp on only one side of the needle shaft, or be embodied by a metal coating on the needle shaft.

Furthermore, protective members can be used which have a clamping means instead of the described engaging means with the radial projection 2a at the needle shaft, so that a continuously smooth needle 2 without a radial projection 2a can be used. Such protective members are described, for example, in U.S. Pat. No. 5,053,017 and U.S. Pat. No. 4,929,241.

The assembly of the protective member preferably takes place in the position of the protective member 3 shown in FIG. 1, so that heat can be applied to the proximal end portion 5b of the shrink tube in the radial direction without hindrance by the needle hub 1. Here, a mechanical distance holder (not shown) can be provided, which determines the distance between the proximal end of the protective member and the proximal end of the shrink tube during the shrinking process. After the shrink tube 5 is assembled, it can be displaced with the protective member 3 into the ready position shown in FIG. 2, in which the proximal end portion 5b abuts at the axially protruding hub portion 1b of the needle hub 1 or at the front end of the ribs 1a. After removal of the protective cap 4, an injection can be carried out and then the shrink tube 5 can be displaced with the protective member 3 into the protective position in FIG. 3.

Various modifications of the described construction are possible. For example, the outer circumference of the shrink tube 5 can also be structured, for example with longitudinally or transversely extending ribs or corrugations. It is also possible to apply lettering or information to the outer circumference of the shrink tube. The shrink tube can also have a sectional shape differing from a circle.

As the middle area of the shrink tube 5 is not changed by heat action, in this area it is also possible to form, for example, openings on the circumference of the shrink tube, through which the protective member 3 positioned inside the shrink tube can have an effect outside the shrink tube, for example by means of the elbow-shaped portions at the distal ends of the spring clip in FIG. 1, which can engage a catheter hub (not shown) in such an embodiment. In such an embodiment, a safeguard against twisting is provided between the shrink tube 5 and the protective member 3, for example in the form that the corners of the proximal transverse wall 3b of the spring clip are held in the material of the shrink tube, or radially protruding members are provided at the protective member 3, preferably at the proximal end portion of the protective member, which serve as a safeguard against twisting and can engage the shrink tube.

In the embodiments described, the radial constrictions or the diametrally reduced portions are formed at the shrink tube in an annular shape continuously over the circumference thereof. However, it is also possible to form shrunk portions on the circumference only at one position or at individual positions, for example by impinging only opposite positions on the shrink tube with heat by means of opposite heating pads. By means of a constriction provided locally on the circumference in such a manner, a retaining portion can be formed for the protective member, which holds the protective member inside the shrink tube 5 in the axial direction.

Figure 9:
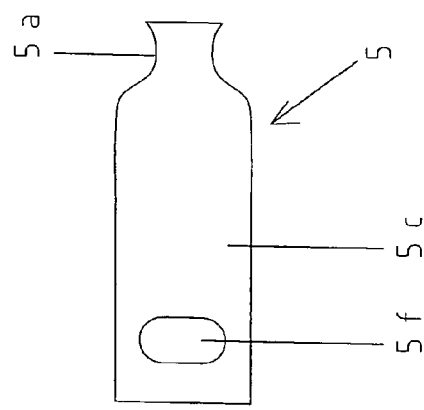
FIG. 9 shows a further embodiment of the deformed shrink tube.

Local deformation of the shrink tube 5 is to be understood as deformation at one or a plurality of locations over the length of the shrink tube and/or along a circumferential line of the shrink tube, wherein over the length of the shrink tube deformation can be also provided only at individual locations on the circumference. In other words, for example, an annular reduction in diameter can be provided, as shown at 5a, 5b or 5d, and in combination with this, a local constriction 5f of the sectional shape can be provided by deformation at an individual position on the circumference at a distance from the annular deformation, as is shown in FIG. 9, in which the area 5f extends into the cross-section of the protective tube by heat action.

Although the disclosure herein refers to certain specific embodiments, it is to be understood that these embodiments are presented by way of example and not by way of limitation. The intent of the foregoing detailed description, although discussing exemplary embodiments, is to be construed to cover all modifications, alternatives, and equivalents of the embodiments as may fall within the spirit and scope of the invention as defined by the claims.

The invention claimed is:

1. A needle assembly comprising:
a needle hub having a distal end attached to a proximal end of a needle having a shaft, a needle tip and a diametrical enlargement proximal of the needle tip;
a displaceable protective member for the needle tip, the protective member disposed on the shaft of the needle and having an engaging section that engages the diametrical enlargement to prevent the protective member from being displaced beyond the needle tip in a needle protective position;
wherein the protective member is surrounded by a tube having a locally reduced diameter by heat action at a proximal end portion of the tube such that the protective member is confined in the tube and spaced from a proximal end edge of the proximal end portion due to interference by the locally reduced diameter; and
wherein in a ready position in which the protective member is spaced from the needle tip, the locally reduced diameter at the proximal end portion forms a stop to maintain a gap between the distal end of the needle hub and the protective member.

2. The needle assembly according to claim 1, wherein the protective member remains axially moveable relative to the tube.

3. The needle assembly according to claim 1, wherein the protective member has a proximal end wall with an opening defining the engaging section having the needle projecting therethrough and at least one resilient arm.

4. The needle assembly according to claim 1, wherein the tube has a locally reduced diameter by heat action at a distal end portion of the tube, spaced from a distal end edge of the distal end portion, which extends distally of the protective member.

5. The needle assembly according to claim 1, wherein the proximal end edge of the proximal end portion of the tube has a diameter that is larger than locally reduced diameter.

6. The needle assembly according to claim 1, wherein the protective member is axially held relative to the tube.

7. The needle assembly according to claim 1, wherein the tube is deformed locally on a circumference of the tube.

8. The needle assembly according to claim 1, wherein at least one end of the tube is provided with an annular radial constriction.

9. The needle assembly according to claim 1, wherein a radial aperture, through which a part of the protective member can act radially outside of the tube, is provided in a non-deformed portion of the tube.

10. The needle assembly according to claim 1, wherein the proximal end edge of the proximal end portion has a diameter and wherein the locally reduced diameter and the diameter of the proximal end edge are generally equal.

11. The needle assembly according to claim 1, wherein the tube has a stiffness in its non-deformed area which resists compression of the shrink tube during handling.

12. The needle assembly according to claim 1, wherein the locally reduced diameter forms a transverse wall that restricts the protective member.

13. The needle assembly according to claim 1, wherein the tube abuts at corners of a rectangular transverse proximal wall of the protective member.

14. The needle assembly according to claim 1, wherein the tube and the protective member confined therein are together displaceable along the needle shaft.

15. The needle assembly according to claim 1, wherein the protective member is formed as a spring clip.

16. The needle assembly according to claim 15, wherein the spring clip has at least one resilient arm with an angled distal end which abuts the needle shaft and lies unrestrained by the tube within the tube in the ready position.

17. A needle assembly comprising:
a needle hub having a distal end attached to a proximal end of a needle having a shaft with a needle tip and a diametrical enlargement proximal of the needle tip;
a displaceable protective member for the needle tip, the protective member disposed on the shaft of the needle and having an engaging section on a proximal wall that engages the diametrical enlargement of the needle shaft to prevent the protective member from being displaced beyond the needle tip to prevent a needle stick injury;
a tube having a tube body having two ends and a center section, said tube body having an interior diameter at the center section and surrounding the protective member;
wherein the tube body has a heat activated locally reduced diameter at a proximal end portion, said locally reduced diameter defining a reduced section for confining the protective member within the center section and for maintaining a gap between a proximal end edge of the proximal end portion and the protective member; and
wherein the reduced section of the tube maintains a gap between the distal end of the needle hub and the protective member.

18. The needle assembly of claim 17, wherein the locally reduced diameter contacts the protective member in a ready position in which the needle tip is exposed for puncturing and a protective position in which the protective member covers the needle tip.

* * * * *